US006437189B1

(12) United States Patent
Prasad et al.

(10) Patent No.: US 6,437,189 B1
(45) Date of Patent: Aug. 20, 2002

(54) SYNTHESIS OF SULFOXIDES VIA SELECTIVE OXIDATION OF SULFIDES WITH A PERBORATE OR A PERCARBONATE

(75) Inventors: Vidyanatha A. Prasad; Peter E. Newallis, both of LeaWood, KS (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 08/990,120

(22) Filed: Dec. 12, 1997

(51) Int. Cl.$^7$ ............... C07C 315/02; C07C 315/06; C07C 317/02; C07D 285/12
(52) U.S. Cl. ......................... 568/27; 548/136
(58) Field of Search ............................ 548/136; 568/27

(56) References Cited

U.S. PATENT DOCUMENTS 3,562,284 A * 2/1971 Newman et al. ............ 548/136
4,724,235 A * 2/1988 Shanklin et al.

OTHER PUBLICATIONS

J. Grant, Ed. Hackh's Chemical Dictionary, $4^{th}$ edition 1969.*
T. Durst, Comprehensive Organic Chemistry, Chapter 11.6, pp. 121–156 vol. 3, 1979.

* cited by examiner

Primary Examiner—T. A. Solola
(74) Attorney, Agent, or Firm—Joseph C. Gil

(57) ABSTRACT

The present invention provides a process for making sulfoxides from sulfides. The process includes the step of selectively oxidizing a sulfide utilizing a perborate or a percarbonate as an oxidizing agent.

23 Claims, No Drawings

SYNTHESIS OF SULFOXIDES VIA SELECTIVE OXIDATION OF SULFIDES WITH A PERBORATE OR A PERCARBONATE

TECHNICAL FIELD OF THE INVENTION

The field of the present invention is the synthesis of sulfoxides. More particularly, the present invention pertains to the selective oxidation of sulfides with a perborate or a percarbonate.

BACKGROUND OF THE INVENTION

Sulfoxides have the general structure $SOR^1R^2$. Sulfoxides can be produced in a variety of ways. By way of example, sulfoxides can be prepared by (a) oxidizing sulfides, (b) transferring sulphinyl groups, (c) rearranging other sulfoxides, (d) rearranging sulphenate esters, and (e) reacting SO with polyenes (See, e.g., Durst, T., in *Comprehensive Organic Chemistry*, Chapter 11.6).

The formation of sulfoxides from the oxidation of sulfides has been accomplished with a wide variety of oxidizing agents: $PhICl_2$, ozone, chromic acid, DABCO $Br_2$, t-BuOOH, $H_2O$, m-$ClC_6H_4CO_3H$, PhIO, $HNO_3$, $NaIO_3$, $N_2O_4$ and BuOCl (Durst, supra). A problem apparent to the use of all of these oxidizing agents is over oxidation of the sulfides to sulfones. In other words, the product of oxidation of a sulfide is a mixture of sulfide, sulfoxide and sulfone.

There continues to be a need in the art, therefore, for a means of selectively oxidizing sulfides to produce sulfoxides without the production of sulfones.

BRIEF SUMMARY OF INVENTION

The present invention provides a process for the selective oxidation of a sulfide to a sulfoxide. The present process results in formation of the sulfoxide and avoids production of other reaction products such as sulfones. The process includes the step of oxidizing a sulfide in a reaction mixture containing a perborate or a percarbonate as an oxidizing agent to form a reaction product that contains the sulfoxide. The perborate or percarbonate oxidizing agent is preferably in the form of an alkali metal perborate or percarbonate salt. The alkali metal is preferably sodium.

Oxidation preferably occurs at a pH of from about 0.5 to about 5.0 and more preferably from about 0.5 to about 1.0. The pH is maintained by adding acid to a mixture of the sulfide and the oxidizing agent. A preferred acid is hydrochloric acid. Oxidation is preferably carried out at a temperature of from about 60° C. to about 90° C. and, more preferably at a temperature of from about 70° C. to about 80° C.

A preferred sulfide for use in the present process is 2-(methylthio)-5-(trifluoromethyl)-1,3,4-thiadiazole. In a preferred embodiment, the 2-(methylthio)-5-(trifluoromethyl)-1,3,4-thiadiazole is dissolved in an aprotic, aromatic solvent such as toluene.

DETAILED DESCRIPTION OF THE INVENTION

The present invention provides a process for making a sulfoxide from a sulfide while avoiding over-oxidation of the sulfide to a sulfone. The controlled oxidation process includes the step of selectively oxidizing the sulfide in a reaction mixture containing perborate or percarbonate as the oxidizing agent.

The oxidizing agent for the selective oxidation is a perborate or a percarbonate salt. Exemplary and preferred such salts are alkali metal salts such as sodium, potassium or lithium salts. Sodium salts are preferred. Thus, preferred oxidizing agents are sodium perborate or sodium percarbonate, both of which can be obtained from commercial sources. The molar ratio of oxidizing agent to sulfide is from about 1:1 to about 3:1. Preferably, that molar ratio is about 2:1.

The oxidation of the sulfide occurs in an acidic environment. Thus, in addition to the sulfide and the oxidizing agent, the reaction mixture contains an acid. The amount of acid used in the reaction mixture is that amount sufficient to maintain the pH of the reaction mixture below a level of about 1.0 during oxidation. Preferably, the pH of the reaction mixture is maintained at a pH level of from about 0.5 to about 1.0. Any suitable acid that does not adversely affect the oxidation reaction can be used. Preferably, mineral acids such as hydrochloric acid, sulfuric acid or nitric acid are used. Hydrochloric acid is most preferred.

The acid can be added either before or after the addition of the oxidizing agent. In a preferred embodiment, the sulfide is mixed with acid (e.g., 10 weight percent HCl) before the addition of perborate or percarbonate. Additional acid may be needed to maintain the pH within the desired range during oxidation.

Oxidation typically occurs at a temperature of from about 60° C. to about 85° C. and, preferably at a temperature of from about 70° C. to about 80° C. unspent oxidizing agent can be recovered and optionally recycled into the reaction mixture. Still further, a process of this invention can include the step of recovering the formed sulfoxide.

Any sulfide can be used in the process of the present invention. A preferred sulfide is 2-(methylthio)-5-(trifluoromethyl)-1,3,4-thiadiazole. When this sulfide is used, the formed sulfoxide is 2-(methylsulfoxyl)-5-(trifluoromethyl)-1,3,4-thiadiazole.

In contrast to the oxidation of sulfides with traditional oxidizing agents (e.g., peroxide), the use of perborate or percarbonate avoids the formation of sulfones and results in the selective, high yield production of sulfoxides in a safe manner.

The following Examples illustrate preferred embodiments of the present invention and are not limiting of the specification and claims in any way.

EXAMPLES

Example 1

Selective Oxidation of 2-(methylthio)-5-(trifluoromethyl)-1,3,4-thiadiazole with Sodium Perborate 100 grams of toluene, 100.11 grams of 2-(methylthio)-5-(trifluoromethyl)-1,3,4-thiadiazole (TDA-sulfide) and 365 grams of 10 weight percent hydrochloric acid (HCl) were mixed together, stirred and heated to a temperature of about 70° C. Discrete portions of sodium perborate (tetrahydrate) were added to the mixture over a 1 hour time period. The total amount of sodium perborate added was 153.86 grams. The pH of the mixture was continually monitored and concentrated HCl added to maintain the pH between 0.5 and 1.0. After completion of the perborate addition, the mixture was cooked for about 30 minutes at 70° C.–75° C. At this time, the conversion of the TDA-sulfide to the TDA-sulfoxide [(2-(methylsulfoxy)-5-(trifluoromethyl)]-1,3,4-thiadiazole)] was complete.

The phases (aqueous and organic) were separated at a temperature of about 70° C. and the aqueous phase was discarded. The organic phase was stripped of toluene using a rotary vacuum evaporator to yield a molten liquor. TDA-sulfoxide was isolated from the molten liquor via flaking. The molten liquor was spread out on a solid surface (aluminum foil), cooled to room temperature and the TDA-sulfoxide allowed to crystallize as aggregate flakes. The purity of formed TDA-sulfoxide was 99.1% as determined using gas or high pressure liquid chromatography. The net yield of TDA-sulfoxide was 98.9%, based on TDA.

Example 2

Selective Oxidation of 2-(methylthio)-5-(trifluoromethyl)-1,3,4-thiadiazole with Sodium Percarbonate 100 grams of toluene, 100.11 grams of 2-(methylthio)-5-(trifluoromethyl)-1,3,4-thiadiazole (TDA-sulfide) and 365 grams of 10 weight percent hydrochloric acid (HCl) were mixed together, stirred and heated to a temperature of about 70° C. Discrete portions of sodium percarbonate were added to the mixture over a 1 hour time period. The total amount of sodium percarbonate added was 1 mole. The pH of the mixture was continually monitored and concentrated HCl added to maintain the pH between 0.5 and 1.0. After completion of the percarbonate addition, the mixture was cooked for about 30 minutes at 70° C.–75° C. At this time, the conversion of the TDA-sulfide to the TDA-sulfoxide [(2-(methylsulfoxy)-5-(trifluoromethyl)-1,3,4-thiadiazole)] was complete.

The phases (aqueous and organic) were separated at a temperature of about 70° C. and the aqueous phase was discarded. The organic phase was stripped of toluene using a rotary vacuum evaporator to yield a molten liquor. TDA-sulfoxide was isolated from the molten liquor via flaking. The molten liquor was spread out on a solid surface (aluminum foil), cooled to room temperature and the TDA-sulfoxide allowed to crystallize as aggregate flakes. The purity of formed TDA-sulfoxide was 98.6% as determined using gas or high pressure liquid chromatography. The net yield of TDA-sulfoxide was 98.5%, based on TDA.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for making a sulfoxide comprising oxidizing a sulfide in a reaction mixture containing a perborate as an oxidizing agent to form a reaction product that contains the sulfoxide, wherein the oxidation occurs at a pH of from about 0.5 to about 5.0.

2. The process of claim 1 wherein the perborate is an alkali metal perborate salt.

3. The process of claim 2 wherein the alkali metal perborate is sodium perborate.

4. The process of claim 1 wherein the pH is from about 0.5 to about 1.0.

5. The process of claim 1 wherein the pH is maintained by adding acid to a mixture of the sulfide and the oxidizing agent.

6. The process of claim 5 wherein the acid is hydrochloric acid.

7. The process of claim 1 wherein oxidation is carried out at a temperature of from about 60° C. to about 90° C.

8. The process of claim 7 wherein the temperature is from about 70° C. to about 80° C.

9. A process of making a sulfoxide comprising oxidizing a sulfide in a reaction mixture containing percarbonate as an oxidizing agent to form a reaction product that contains the sulfoxide, wherein the oxidation occurs at a pH of from about 0.5 to about 5.0.

10. The process of claim 9 wherein the perbcarbonate is an alkali metal perbcarbonate salt.

11. The process of claim 10 wherein the alkali metal perbcarbonate is a sodium perbcarbonate.

12. The process of claim 9 wherein the pH is from about 0.5 to about 1.0.

13. The process of claim 9 wherein the pH is maintained by adding acid to a mixture of the sulfide and the oxidizing agent.

14. The process of claim 13 wherein the acid is hydrochloric acid.

15. The process of claim 9 wherein oxidation is carried out at a temperature of from about 60° C. to about 90° C.

16. The process of claim 15 wherein the temperature is from about 70° C. to about 80° C.

17. The process of claim 1 wherein the sulfide is 2-(methylthio)-5-(trifluoromethyl)-1,3,4-thiadiazole.

18. The process of claim 17 wherein the 2-(methylthio)-5-(trifluoromethyl)-1,3,4-thiadiazole is dissolved in an aprotic, aromatic solvent.

19. The process of claim 18 wherein the solvent is toluene.

20. The process of claim 9 wherein the sulfide is 2-(methylthio)-5-(trifluoromethyl)-1,3,4-thiadiazole.

21. The process of claim 20 wherein the 2-(methylthio)-5-(trifluoromethyl)-1,3,4-thiadiazole is dissolved in an aprotic, aromatic solvent.

22. The process of claim 21 wherein the solvent is toluene.

23. A process of making a sulfoxide comprising oxidizing a sulfide in the presence of sodium perborate at a pH of from about 0.5 to about 1.0 and at a temperature of from about 70° C. to about 80° C.

* * * * *